United States Patent [19]

Munsch et al.

[11] Patent Number: 4,541,829
[45] Date of Patent: Sep. 17, 1985

[54] AUTOMATIC CONNECTION AND DISCONNECTION

[75] Inventors: John M. Munsch, Libertyville; Brant R. Danielsen, Round Lake Beach; Jimmy L. Miller, Waukegan, all of Ill.

[73] Assignee: Baxter Travenol Laboratories, Inc., Deerfield, Ill.

[21] Appl. No.: 600,858

[22] Filed: Apr. 16, 1984

Related U.S. Application Data

[63] Continuation of Ser. No. 416,785, Sep. 10, 1982, abandoned.

[51] Int. Cl.⁴ .......................... A61M 51/14; A61J 5/00
[52] U.S. Cl. ......................................... 604/80; 604/29; 604/411; 222/83; 141/330
[58] Field of Search ...................... 604/27–30, 604/33, 34, 80, 81, 246, 249, 257, 261, 262, 406–408, 410–413, 905; 222/83, 83.5, 89, 129, 145; 285/12; 248/95; 53/469; 141/330, 248; 137/318, 635

[56] References Cited

U.S. PATENT DOCUMENTS

| | | | |
|---|---|---|---|
| 3,413,097 | 11/1968 | Jungner | 141/248 |
| 3,840,011 | 10/1974 | Wright | 604/407 |
| 4,169,474 | 10/1979 | Wagner | 604/407 |
| 4,219,055 | 8/1980 | Wright | 604/407 |
| 4,405,315 | 9/1983 | Handt | 604/29 |

OTHER PUBLICATIONS

Zaharias, "CAPD for the Blind", *Nephrology Nurse*, Mar./Apr. 1981, pp. 53–54.

*Primary Examiner*—Stephen C. Pellegrino
*Assistant Examiner*—Michelle N. Lester
*Attorney, Agent, or Firm*—Paul C. Flattery; Garrettson Ellis

[57] ABSTRACT

Apparatus for removing a first connector from a second connector and reconnecting the first connector with the third connector by mechanical means so that the visually impaired can do it, without touching critical areas where sterility should be retained. The apparatus finds particular use in the field of peritoneal dialysis where the catheter or set connecting to the patient must be disconnected from one container of solution and reconnected to another under the most aseptic conditions possible. A platform is provided having track means for permitting controlled movement of a first retention means between a first position, permitting disconnection between the first and second connectors, and a second position permitting connection between the first and third connectors when the first, second, and third connectors are respectively carried in the first, second, and third retention means.

25 Claims, 9 Drawing Figures

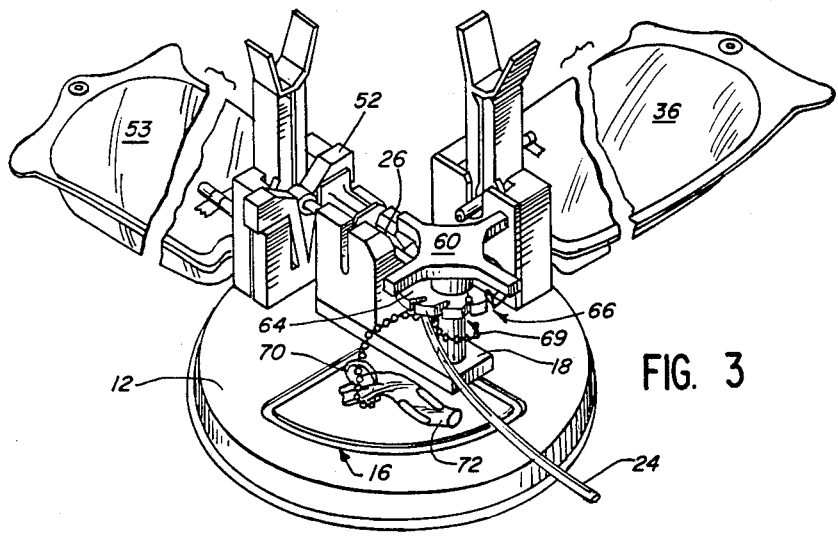
FIG. 3
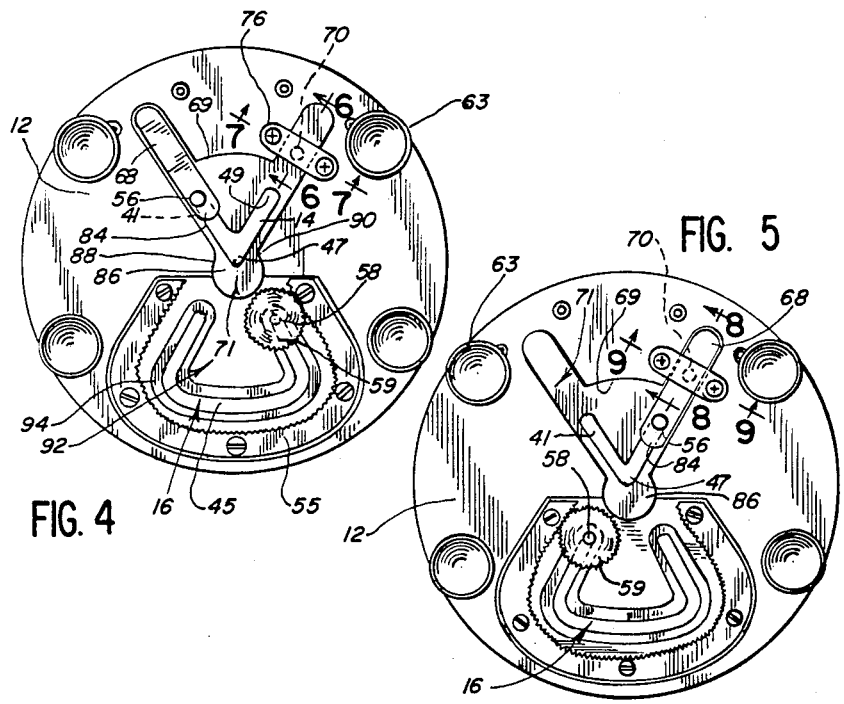
FIG. 4
FIG. 5

AUTOMATIC CONNECTION AND DISCONNECTION

This is a continuation of application Ser. No. 416,785, filed Sept. 10, 1982 now abandoned.

TECHNICAL FIELD AND PRIOR ART

In the various forms of peritoneal dialysis, and particularly continuous ambulatory peritoneal dialysis (CAPD) it is well known that extra effort must be exerted to maintain aseptic conditions during the course of the procedure in which peritoneal dialysis solution is passed into the peritoneal cavity and thereafter removed from the peritoneal cavity. Typical peritoneal dialysis procedures require disconnection and reconnection of a connector which terminates a set communicating with the interior of the peritoneal catheter and connectors on various bags or other containers of peritoneal dialysis solution. The slightest touch of a critical portion of the connector with a contaminated surface is believed to create a significant risk of peritonitis to the patient.

Accordingly, particularly in CAPD where four connections and four disconnections may be made in a day, it becomes desirable to provide a controlled means for disconnecting and reconnecting the various connectors in a manner which will minimize the risk of contamination. Particularly in the case of the visually impaired or patients who exhibit tremors in their hands and the like, there is a significant need for providing such patients with mechanical assistance in making and breaking connections in an aseptic manner during the peritoneal dialysis procedure.

One mechanical device for accomplishing this is the Steri-Track device which has been used and which is described in an article entitled "CAPD for the Blind" from the periodical *Nephrology Nurse,* March/April 1981 pp. 53–54. This device is a self-contained, portable device. When doing bag exchanges, a fresh bag of dialysate is placed into a stationary end of a holder. At this point the protective tab of the bag is removed, and a spike is taken from the discharge bag and fitted into the grooves of a movable plate. The patient now manipulates the sliding plate toward the bag with the result that the spike will plunge into the port of the bag with alleged 98 percent probability.

This, however, only solves a portion of the problem, since contamination can be picked up between the time the spike is removed from the bag of spent dialysate and inserted into the fresh bag. For example, the patient may cause the spike to brush against the contaminated surface while trying to load it into the device.

In accordance with this invention, an apparatus is provided into which the transfer set for peritoneal dialysis or the like, while connected with the bag of spent dialysis solution, can be loaded into the device without breaking of the connection. Thereafter, the breaking of the connection and the making of the new connection can be done in a positive, mechanical manner while the patient can keep his hands entirely away from all of the connectors, so that the chance of accidental contamination by even a blind patient is greatly reduced.

DESCRIPTION OF THE INVENTION

In accordance with this invention, an apparatus is provided for removing a first connector from a second connector and reconnecting the first connector with a third connector. Specifically, the apparatus is contemplated for use in changing peritoneal dialysis solution bag connections, while providing added assurance that the user does not accidentally contaminate the connectors during the bag-changing process.

The apparatus of this invention comprises first, second, and third retention means for respectively carrying first, second, and third connectors. Platform means are provided for carrying the first, second and third retention means, and track means on the platform means are present for permitting controlled movement of the first retention means along the track means between a first position permitting disconnection between the first and second connectors and a second position permitting connection between the first and third connectors, when the first, second, and third connectors are respectively carried in the first, second, and third retention means.

The track means typically may comprise separate forward and rear segments. Means may be provided for movably retaining the first retention means in the forward and rear segments. Each of the forward and rear segments may include first and second end portions which are straight, and respectively parallel to the axis of a second connector and a third connector carried in the second and third retention means. As the result of this, the first retention means moves into and out of its first and second positions in a direction parallel to the carried second and third connectors.

The rear segments of the track means may define an arcuate track portion between its straight end portions, while the forward segment may be V-shaped.

The first retention means may also carry handle and rotatable gear means, while toothed rack means engaging the gear means may be defined along the track means as a part thereof, to permit positive, mechanically controlled movement of the first retention means along the track means.

The handle and rotatable gear means may carry a flexible cable member, for connection to a port protector of the third connector. Thus rotation of the handle and gear means can cause the cable to remove the port protector as the first connector is removed from the second connector.

As an advantage of the device of this invention, all of the set up of the device, the loading of the bags and the peritoneal dialysis set, and the connecting of the port protector with the cable, can all take place before opening of the connections and connectors. Thus, a blind person does not have to worry in this "set up" stage that he may contaminate anything. His hands can explore all areas to be sure that the system is set up. Thereafter, all the operator has to do is to operate the handle means, and the entire disconnection, opening, and reconnection operation can proceed automatically.

Gripping jaws may be provided on the third retention means to grip and transversely press third connectors carried by the third retention means. This has particular advantage for alignment purposes when the connectors are respectively spikes and sleeves adapted for receiving the spike. Typically the first connector may be a spike while the second and third connectors are flexible plastic sleeves of typically conventional design adapted for receiving the spike in sealing manner for connection with the contents of solution bags. The spike will typically have a point on it. In the specific embodiment the point is positioned downwardly. Accordingly, the jaws can squeeze the sleeve which is the target for reconnection with the spike, to, in the specific embodiment, vertically elongate the inner area of the lumen of the spike. This provides a slightly larger vertical component to the target area for the spike, so that the spike will more reliably connect with the lumen of the sleeve and form the desired sealing connection.

Means may also be provided to open the gripping jaws as the first retention means moves into the second position, by means of a cam or the like. As the result of this, the gripping jaws cannot engage a first connector carried in the first retention means, since the jaws are forced open as the first connector comes within range. Also, this means that the third connector can be easily removed from third retention means after connection with the first connector, since the jaws are open in that circumstance.

DESCRIPTION OF THE DRAWINGS

FIG. 3 is a perspective view showing the apparatus in its position connecting the first and third connectors.

FIG. 4 is a bottom plan view of the device, shown in the position of FIG. 1.

FIG. 5 is a bottom plan view of the device, shown in the position of FIG. 3.

DESCRIPTION OF SPECIFIC EMBODIMENT

Figure 1:
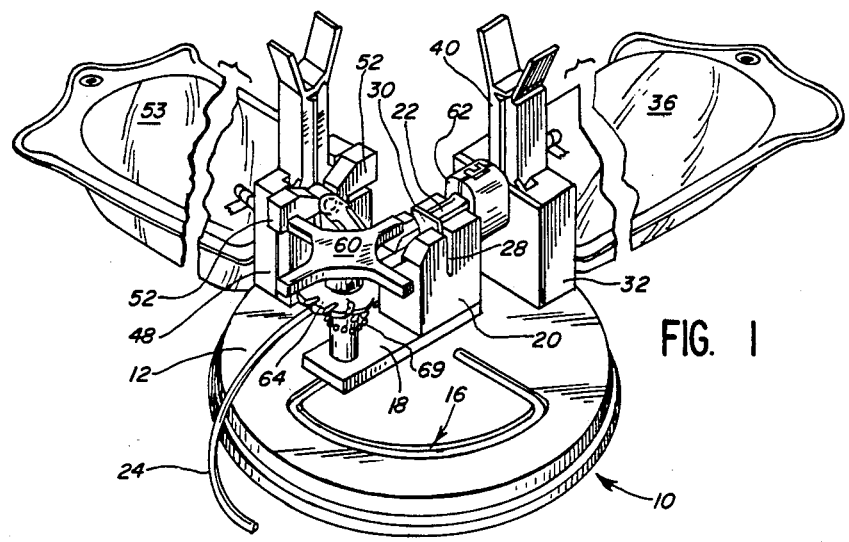
FIG. 1 is a perspective view of the apparatus of this invention in which a peritoneal set in connection with the peritoneal cavity of a patient and two peritoneal dialysis solution bags are emplaced on the apparatus for changing of connection from one bag to another.

Referring to the drawings, apparatus 10 of this application is shown comprising a platform member 12 of milled plastic which defines forward track segment 14 which may be of V shape and rear track segment 16. First retention means 18 is shown to comprise a plate upon which a retainer 20 is positioned for holding a conventional spike connector 22 of a peritoneal dialysis set 24, which may be of a design as currently sold by Travenol Laboratories, Inc. of Deerfield, Ill. Spike connector 22 can fit into slot 26 of retainer 20, also defining transverse slot 28 for receiving a flange 30 of the spike connector.

Second retention means 32 is also provided, being fixed in position on platform 12 in a position so that port 34 of solution bag 36 can project through slot 38. The width of slot 38 may be proportioned so that port 34 fits through with a relatively tight fit in a conventional design of solution bag sold by Travenol Laboratories, Inc., where port 34 defines an outer tube of lesser inner diameter than an inner tube which holds the outer tube. Thus the inner tube of slightly larger inner diameter cannot pass through slot 38. This provides stability against longitudinal motion as spike 22 is withdrawn from port 34.

Port 34 may be closed with a conventional CAPD gripper clamp member 40, of a design sold by Travenol Laboratories, Inc., with enlarged slot 42 being provided in second retention means 32 to receive it. Bag gripper member 40 may be of the design disclosed in U.S. Pat. No. 4,227,730, carrying a flange 44, and transverse slot and bevel 46 may be provided to receive flange 44. This also provides further longitudinal stability to port 34 for ease of removal of spike 22.

Third retention means 48 is also provided, being fixed to platform 12, and is shown to carry third connector 50, which in this embodiment is a tube for receiving spike 22 being attached to fresh solution bag 53. Connector 50 is also closed with another bag gripper clamp 40a, which may be of similar design to bag gripper 40. Alternatively, other kinds of clamps or closures may be used as desired in lieu of bag grippers 40, 40a.

Third retention means 48 carries a pair of spring jaws 52 which may be a one-piece connection through spring members 54 to the remainder of third retention means 48. The purpose of jaws 52 is to properly position port 50, and also press on the end of port 50, which may be made out of flexible plastic, to slightly elongate its inner diameter in the vertical direction. Since the tip of spike 22 has a point which is typically positioned in the downward postion, jaws 52 can cause the inner diameter of port 50 to assume a slight vertical oval shape by the action of cut-outs 53. This improves the quality of port 50 as a target for connection with spike 22, providing greater reliability of connection.

If the point of spike 22 were off at the side rather than at the top or bottom, then it could be desirable for jaws 52 to be rotated 90° or so to achieve the same effect. If a center-point spike is used, then jaws 52 and cut-outs 53 may be designed to hold tubing 50 in a round configuration, rather than an oval one.

Turning to FIG. 4, it can be seen that rear segment 16 of the track means has alongside of it a toothed rack 55. First retention means 18 carries a pair of pins 56, 58, each of which operate respectively in the grooves of track segments 14, 16. Pin 58 carries a rotatable gear 59 which engages with rack 55 and, in turn, pin 58 is connected to handle 60 carried on first retention means 18. Accordingly, as the operator rotates handle 60, gear 59 rotates, traveling along rack 55 and causing first retention means 18 to move.

As can be seen from FIGS. 4 and 5, forward track segment 14 may be V shaped, having straight arms 41, 49. Rear track segment 16, on the other hand, may have end portions 43, 51 which are straight and an arcuate central section 45. Portions 41, 43 and portions 49, 51 are parallel to each other and to the axes respectively of second connector 34 and third connector 50, to permit first retention means 18 to move connector 22 in a colinear manner with the axis of each of connectors 34, 50 when in the proper track portion to do so, for ease of disconnection and reconnection of spike 22.

Feet 63 may also be provided to platform 12.

Accordingly, the apparatus of this invention functions in the following manner:

The system is set up in the manner of FIG. 1. Typically the patient has been wearing bag 36 connected to set 24 under his clothes for a few hours, while the dialysis solution from the bag occupies his peritoneal cavity. The connection between spike 22 and port 34 is protected by hinged casing 62 (FIG. 1), which may be of the design as described in U.S. Pat. No. 4,340,052. After the set up in accordance with FIG. 1 is complete, hinged casing 62 can be removed. The user, who up to this time has been able to handle every aspect of the system, withdraws his hands, touching only handle 60, and begins to rotate the handle. As gear 59 rotates along rack 55, spike 22 is withdrawn from port 34, moving along straight segments 41, 43, respectively, of track sections 14, 16. As shown, straight sections 41, 43 are parallel to the axis of tubular second connector 34, so that spike 22 is withdrawn with ease from tube 34. Thereafter, as handle 60 continues to rotate, the rear of first retention means 18 swings along arcuate section 45 (FIG. 2), while pin 56 pivots in the base of V-shaped section 47 of forward track 14.

Thereafter, as shown in FIG. 3, first retention means 18 is advanced along parallel portions 49, 51 (FIG. 2) of track segments 14, 16 to drive spike 22 into the bore of third connector 50, for connection of set 24 with fresh dialysis solution bag 53 in a manner where no touching of any part of the apparatus is required except for turning of handle 60.

Figure 2:
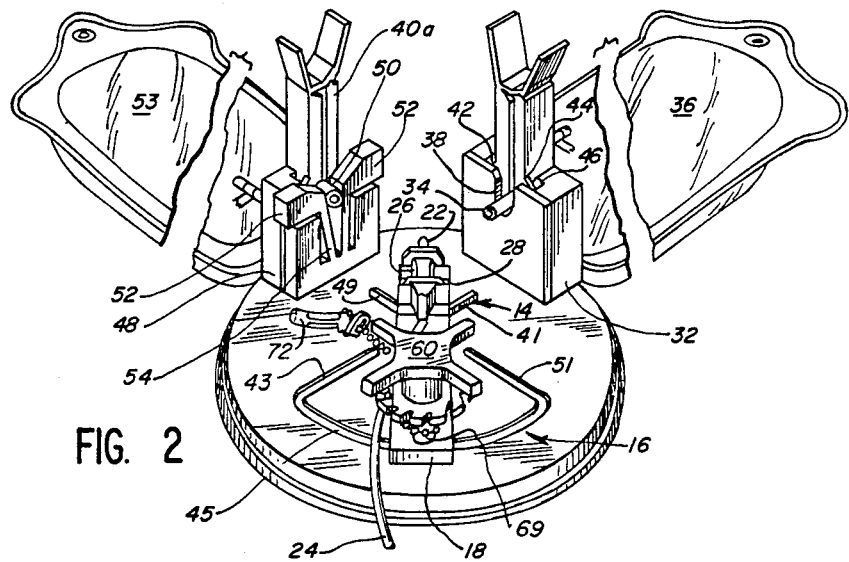
FIG. 2 is a perspective view of the apparatus of this invention in a position midway between disconnection of the first and second connectors and connection of the first and third connectors.

Handle 60 may carry a flange 64 defining a series of slots 66 or other retention means for cable means 69, specifically shown as a chain. Chain 69 may carry a hook or other fastener 70 which may be initially set up to connect to a port protector of third connector 50 which must be removed before connection can be made. This system can be particularly effectively used with the design of port protector used on the peritoneal dialysis solution bags sold by Travenol, which is a plastic sleeve which is peeled off the end of third connector 50. Accordingly, after chain 69 is connected to the port protector 72 as handle 60 is rotated, chain 69 winds about the handle so that tension is applied to port protector 72 causing it to be removed. By the time first retention means 18 has swung about into its second position to bring connector 22 into connecting relation with connector 50, port protector 72 will have been removed and will fall onto platform 12 as shown in FIGS. 2 and 3.

Figure 6:
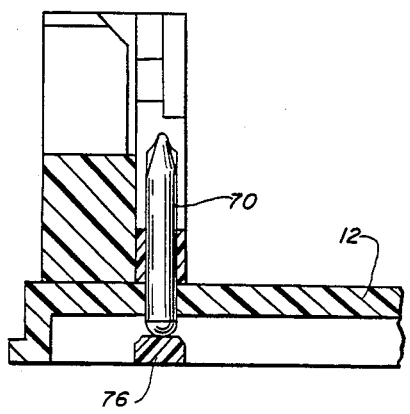
FIG. 6 is a fragmentary sectional view taken along line 6—6 of FIG. 4, with certain portions removed for clarity.
Figure 7:
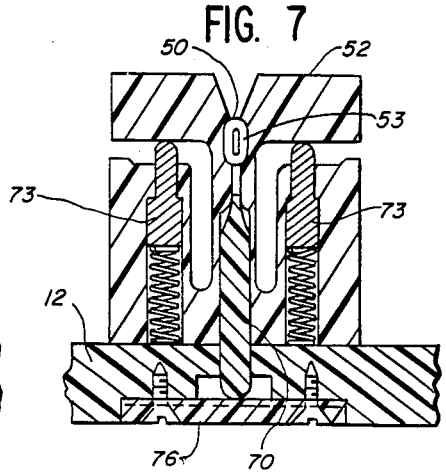
FIG. 7 is a fragmentary sectional view taken along line 7—7 of FIG. 4.

Referring to FIGS. 6 and 7, means are shown to open the gripping jaws as the first retention means moves into the second position. The advantage of this is that the gripping jaws 52 then cannot ever engage first connector 22, when carried in the first retention means 18.

Figure 8:
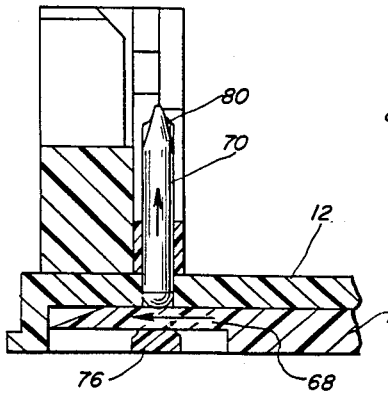
FIG. 8 is a fragmentary sectional view taken along line 8—8 of FIG. 5.
Figure 9:
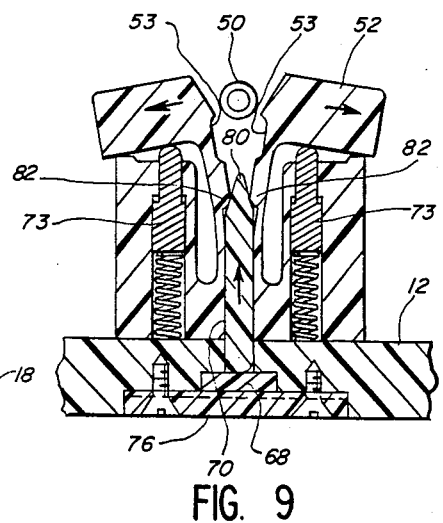
FIG. 9 is a fragmentary sectional view taken along line 9—9 of FIG. 5, showing how jaws 52 are opened when the first retention means moves into the second position.

As shown in FIGS. 4, 8, and 9, first retention means 18 carries a cam foot member 68 on pin 56 (FIG. 4). FIGS. 1, 4, 6 and 7 show the structure of this invention in its first position. When motion is initiated to move the retention means 18 from its first position to the second position, retention means 18 is first withdrawn in an axial manner as previously described. Corresponding to this, cam 68 is withdrawn until it clears wall 69 of cutaway area 71, in which slot 14 resides, to permit cam 68 to be rotated. Thereafter, as retention member 18 is rotated by swinging along arcuate portion 45 of track 16, and also pivoting in slot area 47, cam 68 can correspondingly swing along wall 69, so that as retention member 18 is moved into its second position as shown in FIGS. 3, 5, 8, and 9, cam 68 can occupy its new position as shown in FIG. 5.

As first retention means 18 is withdrawn from its first position, cam member 68 slides rearwardly in cutaway area 71 until rear end 84 of cam foot 68 is positioned in rounded area 86 of cutaway area 71. As stated, retention means 18 is then rotated into alignment with arm 49 of forward track segment 14 and advanced to the configuration of FIGS. 3 and 5. The presence of wall portion 88, which with wall portion 90 defines and substantially surrounds circular portion 86 of cutaway area 71, prevents pin 56 from accidentally slipping again up arm 41 of V-shaped track section 14 as retention means 18 is attempted to be advanced up arm 49 into its second position. While cam foot 68 points toward arm 49, wall portion 88 prevents end 84 of cam foot 68 from moving in a direction that would permit pin 56 from moving in that undesired direction.

Thus, this particular design eliminates the need for a complicated escapement mechanism to assure that cam foot 68 will reliably move between arms 41 and 49 in sequence, without error, as pin 58 is moved back and forth along rack 55 between its two positions, for reliable operation of the system. On the reverse move from the second position back to the first position for reuse of the device of this invention, wall portion 90 of cutaway area 71 performs a similar function, to be sure that pin 56 withdrawing from arm 49 of slot 14 is directed back into slot arm 41 after cam foot 68 is pointed into slot arm 41.

Rack 55 and slot 16 reside in second cutaway area 92, which is typically not as deep a cut as cutaway area 71. A deeper, generally U-shaped cut 94, is then also provided in which slot 16 resides. Thus rack 55 can be recessed with respect to the bottom face of platform member 12. Each of cutaway areas 71, 92, and 94 have generally flat exposed surfaces.

As particularly shown in FIG. 7, jaws 52 are shown gripping port tube 50, with jaws 52 being biased together by the action of spring plungers 73. Accordingly, jaws 52 are constantly biased toward the closed position to force port 50 into its oval cross section, for the reasons described above. Plunger 70 rests between jaws 52, being secured within the structure by strap member 76.

As cam 68 is advanced to its second position (FIGS. 5, 8, and 9), it passes between strap member 76 and plunger 70, moving plunger 70 upwardly as shown particularly in FIG. 8, with the result that jaws 52 are forced open by the action of the tapered end 80 of plunger 70 operating on shoulders 82 of jaws 52, to force jaws 52 to open against the action of spring plungers 73, thereby releasing tube 50 from their grip.

Thus the visually impaired patient or a patient with hand tremors can safely use the device of this invention by himself to make safe changes of peritoneal dialysis solution bags, for independent maintenance of the dialysis patient at home.

The above has been offered for illustrative purposes only and is not intended to limit the scope of the invention of this application, which is as defined in the claims below.

That which is claimed is:

1. Apparatus for removing a first connector from a second connector and reconnecting the first connector with a third connector, which comprises:
   first, second, and third retention means for respectively carrying first, second, and third connectors, each connector defining an axis; platform means for carrying said first, second, and third retention means; and means for operatively coupling said first retention means to said platform and permitting controlled movement thereof along a fixed path, said means thereby permitting controlled movement of said first retention means in a first, essentially radial direction from a first position adjacent the second retention means, said first direction being parallel to the axis of a second connector mounted in the second retention means, permitting disconnection at said first position between first and second connectors, said means also permitting controlled movement in a second, different, essentially raidal direction to a second position adjacent the third retention means, said second direction being parallel to the axis of a third connector mounted in the third retention means, permitting connection at second position between first and third connectors, when said first, second, and third connectors are respectively carried in the first, second, and third retention means.

2. The apparatus of claim 1 in which said means for permitting controlled movement includes track means having first and second end portions which are straight.

3. The apparatus of claim 1 in which said controlled movement permitting means comprises separate forward and rear segments, and means for movably retaining said first retention means in said forward and rear segments.

4. The apparatus of claim 3 in which each of said forward and rear segments include first and second end portions which are straight, and respectively parallel to the axis of a second connector and a third connector carried in the second and third retention means, whereby said first retention means moves into and out of its first and second positions in a direction parallel to said carried second and third connectors.

5. The apparatus of claim 4 in which said rear segment defines an arcuate track portion between the straight end portions thereof.

6. The apparatus of claim 1 in which said first retention means carries handle and rotatable gear means, and toothed rack means engaging said gear means is defined along said controlled movement permitting means, to permit positive, mechanically controlled movement of said first retention means along the controlled movement permitting means.

7. The apparatus of claim 6 in which said handle and rotatable gear means carries engagement means for flexible cable means for connection to a port protector of the third connector, whereby rotation of the handle and gear means causes the cable means to remove the port protector as the first connector is removed from the second connector.

8. The apparatus of claim 1 in which said controlled movement permitting means comprises a pair of slots.

9. The apparatus of claim 1 which is adapted for removing a spike of a peritoneal catheter from one solution bag and inserting it into another solution bag.

10. The apparatus of claim 1 in which gripping jaws are provided on the third retention means to grip and transversely press third connectors carried by the third retention means.

11. The apparatus of claim 10 in which means are provided to open said gripping jaws as the first retention means moves into the second position, whereby said gripping jaws cannot engage a first connector carried in the first retention means and the third connector can be easily removed from the third retention means.

12. The apparatus of claim 3 in which said forward segment is V shaped.

13. Apparatus for removing a first connector from a second connector and reconnecting the first connector with a third connector, which comprises:

first, second, and third retention means for respectively carrying said first, second, and third connectors;

platform means for carrying said first, second, and third retention means;

track means comprising separate forward an rear segments, plus means for movably retaining said first retention means in the forward and rear segments;

handle and rotatable gear means carried by the first retention means, and rack means engaging said gear means defined along one of the segments of said track means to permit positive, mechanically controlled movement of the first retention means along the track means from a first position in a first essentially radial direction permitting disconnection between first and second connectors, and toward a second position in a second essentially radial direction permitting connection between the first and third connectors when said first, second, and third connectors are respectively carried in the first, second, and third retention means.

14. The apparatus of claim 13 in which each of said forward and rear segments include first and second end portions which are straight, essentially radial and respectively parallel to the axes of a second connector and a third connector carried in the second and third retention means, whereby said first retention means moves into and out of its first and second positions in a direction parallel to said carried second and third connectors.

15. The apparatus of claim 14 in which said rear segment defines an arcuate track portion between the straight end portions thereof and the forward segment is V shaped.

16. The apparatus of claim 15 in which said handle and rotatable gear means carries engagement means for flexible cable means for connection to a port protector of the third connector, whereby rotation of the handle and gear means causes the cable means to remove the port protector as the first connector is removed from the second connector.

17. The apparatus of claim 15 in which gripping jaws are provided on the third retention means to grip and transversely press third connectors carried by the third retention means.

18. The apparatus of claim 17 in which means are provided to open said gripping jaws as the first retention means moves into the second position, whereby said gripping jaws cannot engage a first connector carried in the first retention means, and the third connector can be easily removed from the third retention means.

19. The apparatus of claim 18, which is adapted for removing a spike connector of a peritoneal dialysis set from one solution bag and inserting it into another solution bag.

20. Apparatus for removing a first connector from a second connector and reconnecting the first connector with a third connector, which comprises:

first, second, and third retention means for respectively carrying first, second, and third connectors;

platform means for carrying said first, second, and third retention means;

track means on said platform means for permitting controlled movement of said first retention means along said track means between a first position permitting disconnection between first and second connectors, and a second position permitting connection between said first and third connectors, when said first, second, and third connectors are respectively carried in the first, second, and third retention means;

gripping jaws, provided as part of the third retention means to grip and transversely press third connectors carried by the third retention means; cam means carried by the first retention means; and cam activated means provided to open said gripping jaws as the first retention means moves into the second position, whereby the gripping jaws cannot engage the first connector carried in the first retention means, and the third connector can be easily removed from the third retention means in said second position.

21. The apparatus of claim 20 in which said cam means occupies a cutaway portion of said platform means, said cutaway portion defining a wall section defining a portion of a circle, the cam means defining a rear portion which is positioned to impinge against said circular wall portion when moving between the first and second positions to assure proper and alternate sequential motion of said cam means between the first and second positions.

22. Apparatus for removing a first connector from a second connector and reconnecting the first connector with a third connector, which comprises:

first, second, and third retention means for respectively carrying first, second, and third connectors; platform means for carrying said first, second, and third retention means; and means for permitting controlled movement of said first retention means in a first, essentially radial direction from a first position permitting disconnection between first and second connectors, said first direction being parallel to the axis of a second connector mounted in the second retention means, and thereafter to move in a second, different, essentially radial direction to a second position permitting connection between first and third connectors, said second direction being parallel to the axis of a third connector mounted in the third retention means, when said first, second, and third connectors are respectively carried in the first, second, and third retention means; said means for permitting controlled movement including track means and means for movably retaining said first retention means in the track means, said track means including first and second end portions which are straight, extending respectively in said first and second different, essentially radial directions, said track means also defining an arcuate track portion between the straight end portions thereof.

23. The apparatus of claim 22 in which said first retention mean carries handle and rotatable gear means, and toothed rack means engaging said gear means is defined along said track means, to permit positive, mechanically controlled movement of said first retention means along the track means.

24. The apparatus of claim 22 in which gripping jaws are provided on the third retention means to grip and transversely press third connectors carried by the third retention means, means being also provided to open said gripping jaws as the first retention means moves into the second position, whereby said gripping jaws cannot engage a first connector carried in the first retention means, and the third connector can be easily removed from the third retention means.

25. The apparatus of claim 22 which is adapted for removing a spike connector of a peritoneal dialysis set from one solution bag and inserting it into another solution bag.

* * * * *